(12) United States Patent
Gore et al.

US009162974B2

(10) Patent No.: US 9,162,974 B2
(45) Date of Patent: *Oct. 20, 2015

(54) PROCESS FOR THE PREPARATION OF VORINOSTAT

(71) Applicant: GENERICS [UK] LIMITED, Hertfordshire (GB)

(72) Inventors: Vinayak G. Gore, Maharashtra (IN); Madhukar S. Patil, Maharashtra (IN); Rahul A. Bhalerao, Maharashtra (IN); Hemant M. Mande, Maharashtra (IN); Sandeep G. Mekde, Maharashtra (IN)

(73) Assignee: Generics (UK) Limited, Hertfordshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/506,741

(22) Filed: Oct. 6, 2014

(65) Prior Publication Data

US 2015/0018424 A1 Jan. 15, 2015

Related U.S. Application Data

(63) Continuation of application No. 13/124,337, filed as application No. PCT/GB2009/051376 on Oct. 14, 2009, now Pat. No. 8,883,851.

(30) Foreign Application Priority Data

Oct. 15, 2008 (IN) .......................... 1746/KOL/2008

(51) Int. Cl.
| | | |
|---|---|---|
| *A61K 31/19* | (2006.01) | |
| *A01N 37/28* | (2006.01) | |
| *C07C 259/06* | (2006.01) | |
| *A61K 31/167* | (2006.01) | |

(52) U.S. Cl.
CPC ............. *C07C 259/06* (2013.01); *A61K 31/167* (2013.01)

(58) Field of Classification Search
USPC ....................................................... 514/575
See application file for complete search history.

(56) References Cited

U.S. PATENT DOCUMENTS

| | | | |
|---|---|---|---|
| 5,369,108 A | 11/1994 | Breslow et al. | |
| 6,497,820 B1 | 12/2002 | Goetzinger et al. | |
| 2004/0122101 A1 | 6/2004 | Miller et al. | |
| 2008/0132575 A1 | 6/2008 | Wong et al. | |
| 2009/0223286 A1 | 9/2009 | Singh et al. | |
| 2011/0263713 A1 | 10/2011 | Gore et al. | |
| 2011/0269838 A1 | 11/2011 | Gore et al. | |

FOREIGN PATENT DOCUMENTS

| | | |
|---|---|---|
| CA | 2671976 | 9/2003 |
| CA | 2663614 | 4/2008 |
| CA | 2712858 | 8/2009 |
| CN | 1870985 | 11/2006 |
| CN | 101080223 | 11/2007 |
| EP | 1541549 | 6/2005 |
| IN | 2057/KOL/2008 | 11/2008 |
| JP | H11-501025 | 1/1999 |
| JP | 2000-510472 | 8/2000 |
| JP | 2003-514904 | 4/2003 |
| JP | 2003-226680 | 8/2003 |
| JP | 2008-519081 | 6/2008 |
| WO | WO 2005/018578 | 3/2005 |
| WO | WO 2005018578 | 3/2005 |
| WO | WO 2006/127319 | 11/2006 |
| WO | WO 2006127319 | 11/2006 |
| WO | WO 2008039421 | 4/2008 |
| WO | WO 2008042146 | 4/2008 |
| WO | WO 2009/077784 | 6/2009 |
| WO | WO 2009/098515 A1 | 8/2009 |
| WO | WO 2009/111998 | 9/2009 |
| WO | WO 2010061219 | 6/2010 |
| WO | WO 2010061220 | 6/2010 |

OTHER PUBLICATIONS

Gediya Lalji K. et al., "A New Simple and High-Yield Synthesis of Suberoylanilide Hydroxamic Acid and Its Inhibitory Effect Alone or in Combination with Retinoids on Proliferation of Human Prostate Cancer Cells", J. Med. Chem., vol. 48, No. 15, Jan. 1, 2005, pp. 5047-5051, XP009126904, ISSN: 0022-2623.

Harwood and Moody, Experimental Organic Chemistry, Principals and Practice, 1996, pp. 127-136.

Houben-Weyl, "Methods of Organic Chemistry", 2002, pp. 517-537.

Du, et al., "High turbulence liquid chromatography online extraction and tandem mass spectrometry for the simultaneous determination of suberoylanilide hydroxamic acid and its two metabolites in human serum" Rapid Communications in Mass Spectrometry, 2005, vol. 19, pp. 1779-1787.

Mai, Antonello et aL, "A new facile and expeditious synthesis of N-hydroxy-N'-phenyloctanedi amide, a potent inducer of terminal cytodifferentiation", Organic Preparations and Procedures International, Organic Preparation and Procedures Co., Newton Highlands, MA., vol. 33, No. 4, Jan. 1, 2001, pp. 391-394, XP009126915, ISSN: 0030-4948.

Marks PA, Richon VM, Rifkind RA., Histone deacetylase inhibitors: inducers of differentiation or apoptosis of transformed cells. J Natl Cancer Inst. Aug. 2, 2000;92(15):1210-6.

Parise, et al., "A liquid chromatography-electrospray ionization tandem mass spectrometric assay for quantitation of the histone deacetylase inhibitor, vorinostat (suberoylanilide hydroxamicacid, SAHA), and its metabolites in human serum" J Chromatography B, 2006, vol. 840, pp. 108-115.

PCT/GB2009/051376 International Preliminary Report on Patentability and Written Opinion of the International Searching Authority, issued Aug. 3, 2010, 21 pages.

(Continued)

*Primary Examiner* — Shirley V Gembeh

(74) *Attorney, Agent, or Firm* — Scott Woodhouse; Fanelli Haag

(57) ABSTRACT

The present invention relates to an improved process for the preparation of the active pharmaceutical ingredient vorinostat. In particular it relates to a process for preparing vorinostat substantially free from impurities.

11 Claims, No Drawings

(56) References Cited

OTHER PUBLICATIONS

Patel, et al., "Simultaneous determination of decitabine and vorinostat (Suberoylanalide hydroxamic acid, SAHA) by liquid chromatography tandem mass spectrometry for clinical studies", J Chromatography B, 2008, vol. 863, pp. 19-25.

Prescribing information for Zolinza, Merck, & Co., Inc., 2008, 10 pages.

Remington, The Science and Practice of Pharmacy, $21^{st}$ edition, 2006, p. 382.

Stowell, John C. et al., "The Synthesis of N-Hydroxy-N'-phenyloctanediamide and Its Inhibitory Effect on Proliferation of AXC Rat Prostate Cancer Cells", J. Med. Chem., vol. 38, Mar. 15, 1995, pp. 1411-1413, XP002577517.

Wise L D et al., "Assessment of developmental toxicity of Vorinostat, a histone deacetylase inhibitor, in Sprague-Dawley rats and Dutch-belted rabgits", Teratology, Wiley Interscience, US, vol. 80, Jan. 1, 2007, pp. 57-68, XP002529072, ISSN: 1542-0752.

www.geosci extract, "Some Background about X-Ray Diffraction", accessed Nov. 28, 2012, 3 pages.

PROCESS FOR THE PREPARATION OF VORINOSTAT

CROSS-REFERENCE TO RELATED APPLICATIONS

This application is a continuation of U.S. application Ser. No. 13/124,337, filed Apr. 14, 2011, and assigned a 371 Completion Date of Jul. 12, 2011, which is a Section 371 National Stage Application of International Application No. PCT/GB2009/051376, filed Oct. 14, 2009 and published as WO 2010/043904 A2 on Apr. 22, 2010, which claims priority from IN Patent Application No. 1746/KOL/2008, filed Oct. 15, 2008, the contents of which are incorporated herein in their entirety for all purposes.

FIELD OF THE INVENTION

The present invention relates to an improved process for the preparation of the active pharmaceutical ingredient vorinostat. In particular it relates to a process for preparing vorinostat substantially free from impurities.

BACKGROUND OF THE INVENTION

Vorinostat, represented by structural formula (I) and chemically named as N-hydroxy-N'-phenyl-octanediamide or suberoylanilide hydroxamic acid (SAHA), is a member of a larger class of compounds that inhibit histone deacetylases (HDAC). Histone deacetylase inhibitors (HDI) have a broad spectrum of epigenetic activities and vorinostat is marketed, under the brand name Zolinza®, for the treatment of a type of skin cancer called cutaneous T-cell lymphoma (CTCL). Vorinostat is approved to be used when the disease persists, gets worse, or comes back during or after treatment with other medicines. Vorinostat has also been used to treat Sézary's disease and, in addition, possesses some activity against recurrent glioblastoma multiforme.

(I)

Vorinostat was first described in U.S. Pat. No. 5,369,108, wherein four different synthetic routes for the preparation of vorinostat are disclosed (Schemes 1 to 4).

The single step process illustrated in Scheme 1 involves coupling of the diacid chloride of suberic acid with aniline and hydroxylamine hydrochloride. However, the yield of this reaction is only 15-30%.

Scheme 1

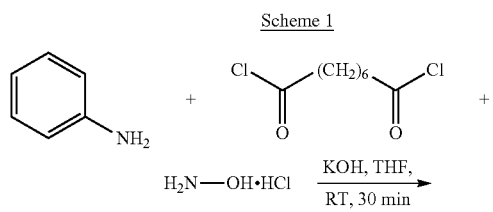

The multistep process illustrated in Scheme 2 begins with the monomethyl ester of suberic acid, which undergoes conversion to the corresponding acid chloride. Further coupling with aniline gives the methyl ester of suberanilic acid. Hydrolysis of the ester and further coupling with benzyl protected hydroxylamine gives benzyl protected vorinostat which on deprotection gives vorinostat.

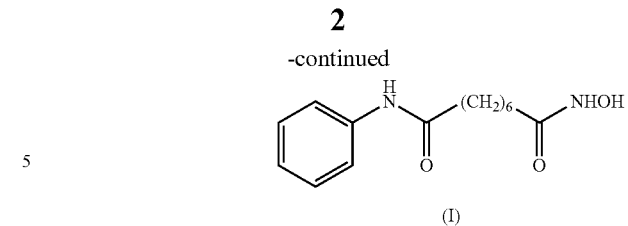

(I)

Scheme 2

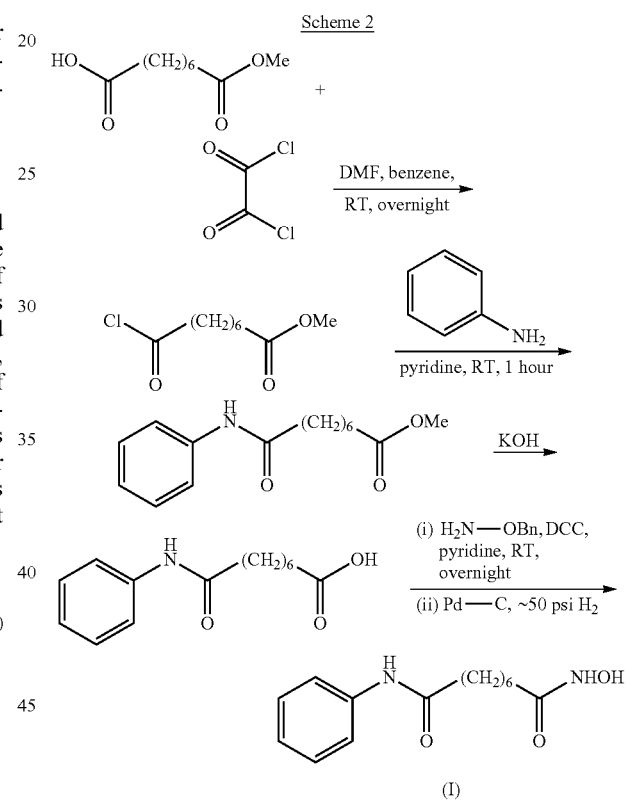

(I)

In addition to the disadvantage of being a five-step process with overall yields reported as 35-65%, this process suffers from further disadvantages such as the use of the expensive monomethyl ester of suberic acid.

Scheme 3

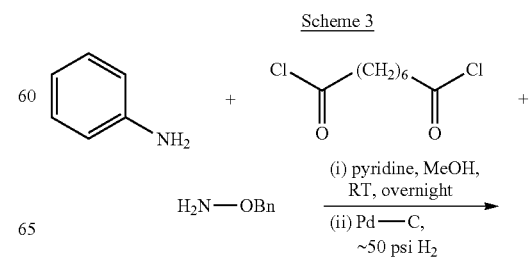

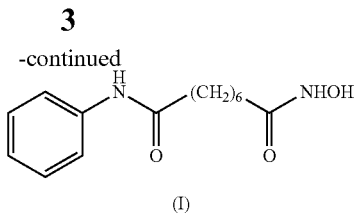

(I)

The two step process illustrated in Scheme 3 involves coupling of the diacid chloride of suberic acid with aniline and O-benzyl hydroxylamine and then deprotection. However, the overall yield of this reaction is only 20-35%.

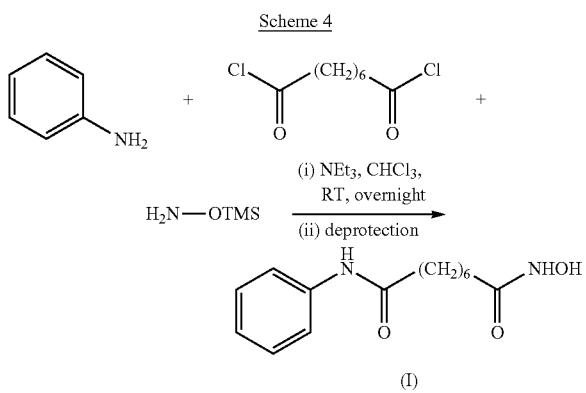

The process illustrated in Scheme 4 is similar to that illustrated in Scheme 3, with the exception that O-trimethylsilyl hydroxylamine was used instead of O-benzyl hydroxylamine. The overall yield of this reaction is reported as 20-33%.

Another process for the preparation of vorinostat has been reported in J. Med. Chem., 1995, vol. 38(8), pages 1411-1413. The reported process, illustrated in Scheme 5, begins with the conversion of suberic acid to suberanilic acid by a high temperature melt reaction. Suberanilic acid is further converted to the corresponding methyl ester using Dowex resin and the methyl ester of suberanilic acid thus formed is converted to vorinostat by treatment with hydroxylamine hydrochloride. However, this process employs high temperatures (190° C.) in the preparation of vorinostat which adds to the inefficiency and high processing costs on commercial scale. The high temperatures also increase the likelihood of impurities being formed during manufacture and safety concerns. The overall yield reported was a poor 35%.

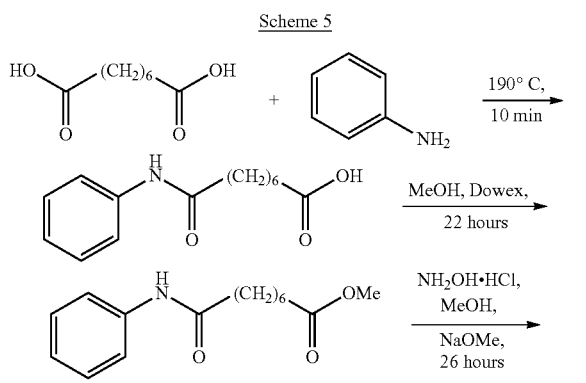

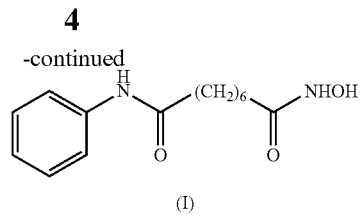

(I)

Another process for the preparation of vorinostat has been reported in OPPI Briefs, 2001, vol. 33(4), pages 391-394. The reported process, illustrated in Scheme 6, involves conversion of suberic acid to suberic anhydride, which on treatment with aniline gives suberanilic acid. Coupling of this suberanilic acid with ethyl chloroformate gives a mixed anhydride which upon treatment with hydroxylamine gives vorinostat in an overall yield of 58%. In the first step, there is competition between the formation of suberic anhydride and the linear anhydride and consequently isolation of pure suberic anhydride from the reaction mixture is very difficult. This process step is also hindered by the formation of process impurities and competitive reactions. In the second step, there is formation of dianilide by reaction of two moles of aniline with the linear anhydride. In the third step, suberanilic acid is an inconvenient by-product as the suberanilic acid is converted to a mixed anhydride with ethyl chloroformate, which is highly unstable and is converted back into suberanilic acid. Consequently, it is very difficult to obtain pure vorinostat from the reaction mixture. Although the reported yield was claimed to be 58%, when repeated a yield of only 38% was obtained.

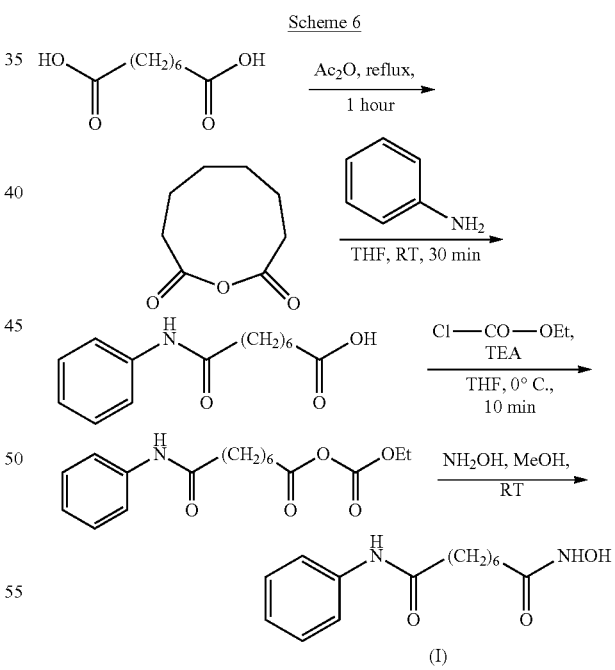

A further process for the preparation of vorinostat has been reported in J. Med. Chem., 2005, vol. 48(15), pages 5047-5051. The reported process, illustrated in Scheme 7, involves conversion of monomethyl suberate to monomethyl suberanilic acid, followed by coupling with hydroxylamine hydrochloride to afford vorinostat in an overall yield of 79%. However, the process uses the expensive monomethyl ester of suberic acid as starting material.

Scheme 7

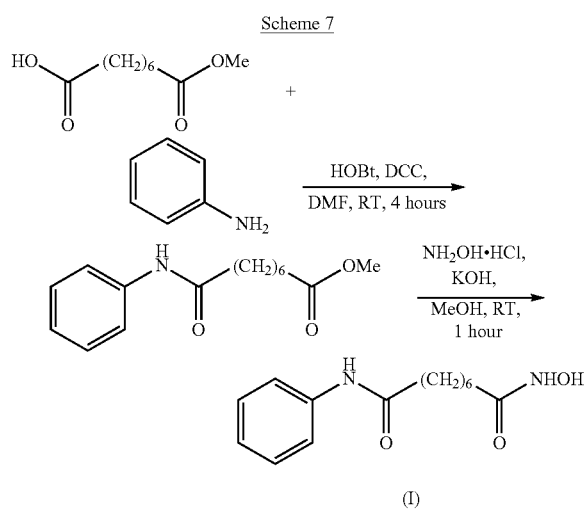

In conclusion, the major disadvantages of the processes disclosed in the prior art for the preparation of vorinostat can be summarised as follows:

- The reaction schemes can involve lengthy process steps to obtain vorinostat and/or are low yielding.
- The reagents used in the processes can be very expensive and not cost effective for commercial manufacture.
- The product is obtained only after column chromatography or extensive purification steps and this reduces the overall yield and puts severe restrictions on the feasibility of the process for scale-up to commercial production.
- All the processes generally require isolation and/or purification of reaction intermediates.

In view of the importance acquired by vorinostat for the treatment of cancer, there is a great need for developing an alternative, relatively simple, economical and commercially feasible process for the synthesis of vorinostat with commercially acceptable yield and high purity.

The present inventors have surprisingly found that vorinostat can be prepared with very high purity employing a simple, efficient process starting with the readily available precursor suberic acid.

OBJECT OF THE INVENTION

It is therefore an object of the present invention to provide a simple, economical and commercially feasible process for the synthesis of high purity vorinostat with commercially acceptable yield.

SUMMARY OF THE INVENTION

The term "vorinostat" as used herein throughout the description and claims means vorinostat and/or any salt, solvate or polymorph thereof.

For the purposes of the present invention, a compound is "substantially pure" if it comprises less than 1% impurity by HPLC, preferably less than 0.5%, preferably less than 0.3%, preferably less than 0.2%, preferably less than 0.1%.

The present invention provides an efficient and economical synthesis of vorinostat which is high yielding and affords the product with very high purity on a commercial scale, whilst avoiding the need for cumbersome purification techniques of the final product or of any synthetic intermediates.

A first aspect of the present invention provides a process for the preparation of vorinostat comprising:
(a) reacting suberic acid with aniline, or a salt thereof, to form suberanilic acid; and
(b) reacting the suberanilic acid formed in step (a) with hydroxylamine, or a salt thereof.

Preferably, the process according to the first aspect of the present invention comprises the use of a coupling agent in step (a). Preferably, the coupling agent in step (a) is not a haloformate. Preferably, the coupling agent in step (a) is selected from a carbodiimide, a 1,1'-carbonyl compound, or a mixture thereof. Preferably, the coupling agent in step (a) is selected from 1,3-dicyclohexylcarbodiimide (DCC); 1,1'-carbonyldiimidazole (CDI); 1-ethyl-3-(3-dimethylaminopropyl)carbodiimide hydrochloride (water soluble carbodiimide hydrochloride, WSC.HCl); 1,3-diisopropylcarbodiimide (DIC); or a mixture thereof.

Most preferably, the coupling agent in step (a) is a mixture of 1,3-dicyclohexylcarbodiimide (DCC) and 1,1'-carbonyldiimidazole (CDI). Preferably, the mixture of CDI and DCC used in step (a) is in a molar ratio range of 0.1:10 to 10:0.1 CDI:DCC, more preferably in a molar ratio range of 1:5 to 5:1 CDI:DCC, even more preferably in a molar ratio range of 1:2 to 2:1 CDI:DCC, and most preferably in a molar ratio of about 1:1.6 CDI:DCC.

Preferably, the total amount of coupling agent used in step (a) with respect to the suberic acid is between 1 to 5 molar equivalents, more preferably between 1 to 3 molar equivalents, even more preferably between 1 to 1.5 molar equivalents, and most preferably is about 1.3 molar equivalents.

Preferably, in a process according to the first aspect of the present invention, step (a) is carried out in an organic solvent, preferably where the organic solvent is selected from dimethylformamide (DMF), tetrahydrofuran (THF), dichloromethane (DCM), acetonitrile, 1,2-dichlorobenzene, ethanol or mixtures thereof. Most preferably, the organic solvent used in step (a) is THF.

Preferably, the total amount of aniline, or its salt, used in step (a) of the process of the first aspect of the present invention, with respect to the suberic acid is about 1 molar equivalent.

Preferably, in a process according to the first aspect of the present invention, step (a) is carried out at a temperature of between 10-60° C., more preferably at a temperature of between 15-40° C., and most preferably at a temperature of between 25-30° C.

Preferably, the process according to the first aspect of the present invention comprises the use of a coupling agent in step (b). Preferably, the coupling agent in step (b) is not a haloformate. Preferably, the coupling agent in step (b) is selected from a carbodiimide, a 1,1'-carbonyl compound, or a mixture thereof. Preferably, the coupling agent in step (b) is selected from 1,3-dicyclohexylcarbodiimide (DCC); 1,1'-carbonyldiimidazole (CDI); 1-ethyl-3-(3-dimethylaminopropyl)carbodiimide hydrochloride (water soluble carbodiimide hydrochloride, WSC.HCl); 1,3-diisopropylcarbodiimide (DIC); or a mixture thereof. Most preferably, the coupling agent in step (b) is 1,1'-carbonyldiimidazole (CDI).

Preferably, the total amount of coupling agent used in step (b) with respect to the suberanilic acid is between 1 to 5 molar equivalents, more preferably between 1 to 3 molar equivalents, and most preferably is about 2 molar equivalents.

Preferably, in a process according to the first aspect of the present invention, step (b) is carried out in an organic solvent, preferably where the organic solvent is selected from dimethylformamide (DMF), tetrahydrofuran (THF), dichloromethane (DCM), acetonitrile, 1,2-dichlorobenzene, ethanol or mixtures thereof. Most preferably, the organic solvent used in step (b) is DMF.

Preferably, in a process according to the first aspect of the present invention, in step (b), hydroxylamine is used in the form of a salt, most preferably the hydrochloride salt.

Preferably, the total amount of hydroxylamine, or its salt, used in step (b) of the process of the first aspect of the present invention, with respect to the suberanilic acid is between 1 to 10 molar equivalents, more preferably between 1 to 6 molar equivalents, even more preferably between 2 to 5 molar equivalents, and most preferably is about 4 molar equivalents.

Preferably, in a process according to the first aspect of the present invention, step (b) is carried out at a temperature of between 10-60° C., more preferably between 15-40° C., and most preferably between 25-30° C.

Preferably, in a process according to the first aspect of the present invention, step (a) and step (b) are carried out in the same organic solvent; preferably selected from dimethylformamide (DMF), tetrahydrofuran (THF), dichloromethane (DCM), acetonitrile, 1,2-dichlorobenzene, ethanol, or a mixture thereof; more preferably selected from THF, DMF, or a mixture thereof.

Preferably, in a process according to the first aspect of the present invention an activating agent is used in step (a) and/or step (b). Preferably, the activating agent is selected from cyanuric chloride, cyanuric fluoride, catecholborane, or a mixture thereof. The activating agent is preferably used in combination with the coupling agent.

A second aspect of the present invention provides a process for the preparation of vorinostat comprising:

(a') reacting suberic acid with hydroxylamine, or a salt thereof, to form N-hydroxy-7-carboxy-heptanamide; and (b') reacting the N-hydroxy-7-carboxy-heptanamide formed in step (a') with aniline, or a salt thereof.

Preferably, the process according to the second aspect of the present invention comprises the use of a coupling agent in step (a'). Preferably, the coupling agent in step (a') is not a haloformate. Preferably, the coupling agent in step (a') is selected from a carbodiimide, a 1,1'-carbonyl compound, or a mixture thereof. Preferably, the coupling agent in step (a') is selected from 1,3-dicyclohexylcarbodiimide (DCC); 1,1'-carbonyldiimidazole (CDI); 1-ethyl-3-(3-dimethylaminopropyl)carbodiimide hydrochloride (water soluble carbodiimide hydrochloride, WSC.HCl); 1,3-diisopropylcarbodiimide (DIC); or a mixture thereof. Most preferably, the coupling agent in step (a') is 1,1'-carbonyldiimidazole (CDI).

Preferably, the total amount of coupling agent used in step (a') with respect to the suberic acid is between 1 to 5 molar equivalents, more preferably between 1 to 3 molar equivalents, even more preferably between 1 to 1.5 molar equivalents, and most preferably is about 1.3 molar equivalents.

Preferably, in a process according to the second aspect of the present invention, step (a') is carried out in an organic solvent, preferably where the organic solvent is selected from dimethylformamide (DMF), tetrahydrofuran (THF), dichloromethane (DCM), acetonitrile, 1,2-dichlorobenzene, ethanol or mixtures thereof. Most preferably, the organic solvent used in step (a') is DMF.

Preferably, in a process according to the second aspect of the present invention, in step (a'), hydroxylamine is used in the form of a salt, most preferably the hydrochloride salt.

Preferably, the total amount of hydroxylamine, or its salt, used in step (a') of the process of the second aspect of the present invention, with respect to the suberic acid is about 1 molar equivalent.

Preferably, in a process according to the second aspect of the present invention, step (a') is carried out at a temperature of between 10-60° C., more preferably between 15-40° C., and most preferably between 25-30° C.

Preferably, the process according to the second aspect of the present invention comprises the use of a coupling agent in step (b'). Preferably, the coupling agent in step (b') is not a haloformate. Preferably, the coupling agent in step (b') is selected from a carbodiimide, a 1,1'-carbonyl compound, or a mixture thereof. Preferably, the coupling agent in step (b') is selected from 1,3-dicyclohexylcarbodiimide (DCC); 1,1'-carbonyldiimidazole (CDI); 1-ethyl-3-(3-dimethylaminopropyl)carbodiimide hydrochloride (water soluble carbodiimide hydrochloride, WSC.HCl); 1,3-diisopropylcarbodiimide (DIC); or a mixture thereof.

Most preferably, the coupling agent in step (b') is a mixture of 1,3-dicyclohexylcarbodiimide (DCC) and 1,1'-carbonyldiimidazole (CDI). Preferably, the mixture of CDI and DCC used in step (b') is in a molar ratio range of 0.1:10 to 10:0.1 CDI:DCC, more preferably in a molar ratio range of 1:5 to 5:1 CDI:DCC, even more preferably in a molar ratio range of 1:2 to 2:1 CDI:DCC, and most preferably in a molar ratio of about 1:1.6 CDI:DCC.

Preferably, the total amount of coupling agent used in step (b') with respect to the N-hydroxy-7-carboxy-heptanamide is between 1 to 5 molar equivalents, more preferably between 1 to 3 molar equivalents, even more preferably between 1 to 1.5 molar equivalents, and most preferably is about 1.3 molar equivalents.

Preferably, in a process according to the second aspect of the present invention, step (b') is carried out in an organic solvent, preferably where the organic solvent is selected from dimethylformamide (DMF), tetrahydrofuran (THF), dichloromethane (DCM), acetonitrile, 1,2-dichlorobenzene, ethanol or mixtures thereof. Most preferably, the organic solvent used in step (b') is THF.

Preferably, the total amount of aniline, or its salt, used in step (b') of the process of the second aspect of the present invention, with respect to the N-hydroxy-7-carboxy-heptanamide is between 1 to 10 molar equivalents, more preferably between 1 to 6 molar equivalents, and most preferably between 1 to 2 molar equivalents.

Preferably, in a process according to the second aspect of the present invention, step (b') is carried out at a temperature of between 10-60° C., more preferably at a temperature of between 15-40° C., and most preferably at a temperature of between 25-30° C.

Preferably, in a process according to the second aspect of the present invention, step (a') and step (b') are carried out in the same organic solvent; preferably selected from dimethylformamide (DMF), tetrahydrofuran (THF), dichloromethane (DCM), acetonitrile, 1,2-dichlorobenzene, ethanol, or a mixture thereof; more preferably selected from THF, DMF, or a mixture thereof.

Preferably, in a process according to the second aspect of the present invention an activating agent is used in step (a') and/or step (b'). Preferably, the activating agent is selected from cyanuric chloride, cyanuric fluoride, catecholborane, or a mixture thereof. The activating agent is preferably used in combination with the coupling agent.

Preferably, the process according to the first or second aspect of the present invention is carried out at a temperature of less than 170° C., preferably less than 130° C., preferably less than 100° C., more preferably less than 70° C.

Preferably, any reaction intermediates of the process according to the first or second aspect of the present invention are not purified. Preferably, the process according to the first or second aspect of the present invention is carried out without isolating any reaction intermediates.

Preferably, the process according to the first or second aspect of the present invention is carried out without the use of chromatography.

Preferably, the process according to the first or second aspect of the present invention is carried out on an industrial scale, preferably to obtain vorinostat in batches of 100 g, 500 g, 1 kg, 5 kg, 10 kg, 25 kg or more.

Preferably, the vorinostat is obtained in a yield of 30% or more, preferably 40% or more, preferably 45% or more, preferably 50% or more, from suberic acid.

Preferably, in a process according to the first or second aspect of the present invention, vorinostat is obtained with an HPLC purity of more than 99%, more preferably vorinostat is obtained with an HPLC purity of more than 99.5%, even more preferably vorinostat is obtained with an HPLC purity of more than 99.8%, and most preferably vorinostat is obtained with an HPLC purity of more than 99.9%.

In a third aspect of the present invention, there is provided vorinostat as prepared according to a process according to the first or second aspect of the present invention.

In a fourth aspect of the present invention, there is provided substantially pure vorinostat as prepared according to a process according to the first or second aspect of the present invention.

In a fifth aspect of the present invention, there is provided substantially pure vorinostat.

Preferably, the vorinostat according to the third, fourth or fifth aspects of the present invention is suitable for use in medicine, preferably for treating cancer, preferably skin cancer, more preferably cutaneous T-cell lymphoma (CTCL).

In a sixth aspect of the present invention, there is provided a pharmaceutical composition comprising the vorinostat according to the third, fourth or fifth aspects of the present invention. Preferably, the pharmaceutical composition according to the sixth aspect of the present invention is suitable for treating cancer, preferably skin cancer, more preferably cutaneous T-cell lymphoma (CTCL).

In a seventh aspect of the present invention, there is provided the use of the vorinostat according to the third, fourth or fifth aspects of the present invention and the use of the pharmaceutical composition according to the sixth aspect of the present invention, in the manufacture of a medicament for the treatment of cancer. Preferably the medicament is suitable for the treatment of skin cancer, most preferably the treatment of cutaneous T-cell lymphoma (CTCL).

In an eighth aspect of the present invention, there is provided a method of treating cancer, comprising administering to a patient in need thereof a therapeutically effective amount of the vorinostat according to the third, fourth or fifth aspects of the present invention or a therapeutically effective amount of the pharmaceutical composition according to the sixth aspect of the present invention. Preferably, the method is for the treatment of skin cancer, most preferably the treatment of cutaneous T-cell lymphoma (CTCL). Preferably, the patient is a mammal, preferably a human.

DETAILED DESCRIPTION OF THE INVENTION

The present inventors have surprisingly found that vorinostat can be prepared with commercially acceptable yield and purity employing an extremely convenient process starting from suberic acid.

The present inventors explored the idea of reacting suberic acid directly and sequentially with aniline and hydroxylamine, in either order. The present inventors found that this direct reaction was possible using coupling agents for selective activation of the carboxyl functional groups in suberic acid. Surprisingly, the direct reactions were high yielding and afforded intermediates and products with very high purity.

Suberanilic acid was prepared by the direct reaction of suberic acid and aniline, very efficiently with good yields and purity, using coupling agents such as 1,3-dicyclohexylcarbodiimide (DCC); 1,1'-carbonyldiimidazole (CDI); 1-ethyl-3-(3-dimethylaminopropyl)carbodiimide hydrochloride (water soluble carbodiimide hydrochloride, WSC.HCl); 1,3-diisopropylcarbodiimide (DIC); or a mixture thereof.

Surprisingly, it was found that the use of 1,3-dicyclohexylcarbodiimide (DCC) and 1,1'-carbonyldiimidazole (CDI) in combination for the coupling of suberic acid and aniline controlled the formation of impurities to afford a very pure product and suberanilic acid was obtained with high yield (60-65%) and very high purity (typically greater than 99.5% as measured by HPLC).

In a second stage, initial attempts to convert suberanilic acid to vorinostat by using prior art methods such as reacting suberanilic acid with methyl chloroformate and hydroxylamine afforded poor yields and high levels of impurities. Consequently, even with repeated purification, the ICH controlled impurity profile for vorinostat could not be obtained.

However, the present inventors found that they could control impurity formation, in the conversion of suberanilic acid to vorinostat, by using coupling agents such as CDI, DCC, WSC.HCl or DIC to yield vorinostat with very high purity (typically greater than 99.5% as measured by HPLC).

Therefore, in a preferred embodiment, the present inventors have found that suberanilic acid can be reacted with commercially available hydroxylamine hydrochloride, using a coupling agent such as CDI, in a polar solvent such as DMF or THF, to afford vorinostat having a purity of greater than 99.5%.

Preferably, the vorinostat prepared by the process according to the present invention can be further purified by crystallization from a suitable solvent or mixture of solvents.

A preferred embodiment of the first aspect of the present invention is illustrated in Scheme 8.

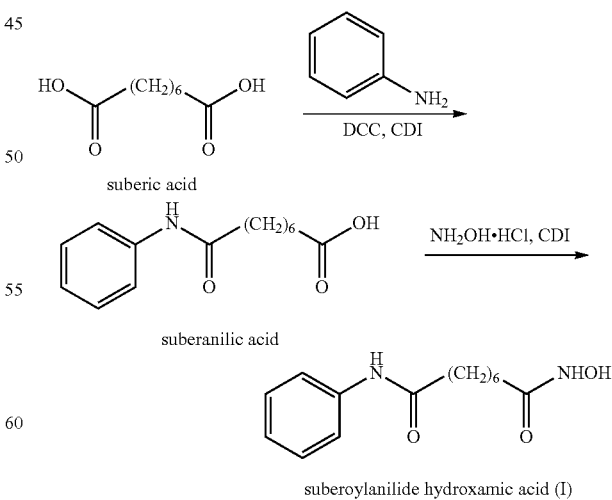

Scheme 8

Optionally, an activating agent can be used in step (a) and/or step (b) to afford products with high yields and purity. Preferably, the activating agent is selected from cyanuric chloride, cyanuric fluoride, catecholborane, or a mixture thereof. The activating agent is preferably used in combination with the coupling agent.

A preferred embodiment of the process according to the first aspect of the present invention comprises the following steps:
(i) taking a mixture of THF, CDI and DCC;
(ii) adding suberic acid;
(iii) adding aniline in THF to the solution from step (ii);
(iv) stirring at 25-30° C.;
(v) filtering off the solid dicyclohexyl urea formed in the reaction;
(vi) concentrating the filtrate in vacuo;
(vii) adding a solution of KOH in water;
(viii) filtering off the solid by-product;
(ix) heating the filtrate;
(x) adding aq. HCl;
(xi) isolating suberanilic acid;
(xii) mixing the suberanilic acid and CDI in DMF;
(xiii) adding hydroxylamine hydrochloride as solid to the mixture from step (xii);
(xiv) isolating vorinostat from the mixture obtained in step (xiii);
(xv) adding acetonitrile and aq. ammonia to the vorinostat from step (xiv);
(xvi) heating the mixture;
(xvii) cooling the mixture to 20-27° C.; and
(xviii) isolating pure vorinostat from the mixture obtained in step (xvii).

Preferably, by utilising the same organic solvent in steps (a) and (b), pure vorinostat can be obtained without isolation of any synthetic intermediate(s).

A preferred embodiment of the second aspect of the present invention is illustrated in Scheme 9.

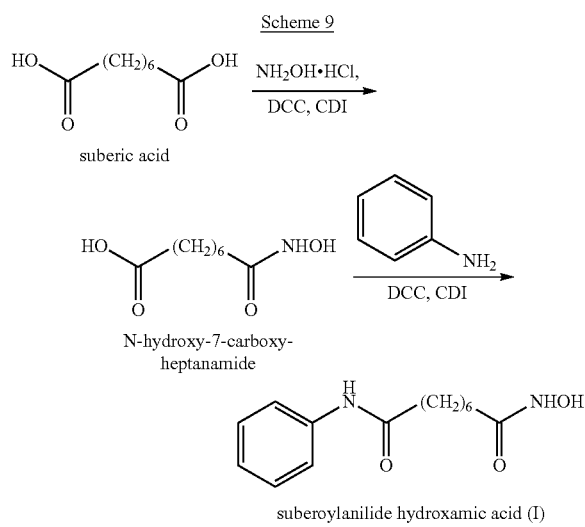

The process according to the first or second aspect of the present invention is a very short, efficient process for the production of substantially pure vorinostat with no requirement for cumbersome purification techniques. Therefore the process of the present invention is extremely suitable for commercial production of substantially pure vorinostat.

The pharmaceutical composition according to the sixth aspect of the present invention can be a solution or suspension, but is preferably a solid oral dosage form. Preferred oral dosage forms in accordance with the invention include tablets, capsules and the like which, optionally, may be coated if desired. Tablets can be prepared by conventional techniques, including direct compression, wet granulation and dry granulation. Capsules are generally formed from a gelatine material and can include a conventionally prepared granulate of excipients.

The pharmaceutical composition according to the present invention typically comprises one or more conventional pharmaceutically acceptable excipient(s) selected from the group comprising a filler, a binder, a disintegrant, a lubricant and optionally further comprises at least one excipient selected from colouring agents, adsorbents, surfactants, film-formers and plasticizers.

If the solid pharmaceutical formulation is in the form of coated tablets, the coating may be prepared from at least one film-former such as hydroxypropyl methyl cellulose, hydroxypropyl cellulose or methacrylate polymers which optionally may contain at least one plasticizer such as polyethylene glycols, dibutyl sebacate, triethyl citrate, and other pharmaceutical auxiliary substances conventional for film coatings, such as pigments, fillers and others.

The details of the invention, its objects and advantages are illustrated below in greater detail by non-limiting examples.

EXAMPLE 1

Stage 1: Conversion of Suberic Acid to Suberanilic Acid

A mixture of CDI (0.5 eq) and DCC (0.8 eq) in THF (15 vol) was stirred for 1 hour at 25-30° C. Suberic acid (1 eq) and aniline (1 eq) in THF (1 vol) was added and the mixture stirred for a further 16-20 hours. The solid by-product was removed by filtration and the filtrate was concentrated in vacuo at 50° C. The solid residue obtained was treated with a solution of KOH (2 eq) in water (10 vol) and stirred for 30 minutes at 25-30° C. and any solid by-product formed was removed by filtration. The filtrate obtained was heated at 60° C. for 3-4 hours and cooled to 20° C. before addition of an aqueous solution of HCl (17.5%, 3 vol). The mixture was stirred for 30 minutes and the solid filtered, washed with water (2×5 vol) and dried under vacuum at 60-65° C.
Molar Yield=60-65%
Purity by HPLC=99.5%

Stage 2: Conversion of Suberanilic Acid to Crude Vorinostat

The suberanilic acid (1 eq) obtained in stage 1 was dissolved in DMF (5 vol) and CDI (2 eq) was added at 25-30° C. and maintained for 30 minutes under stirring. Hydroxylamine hydrochloride (4 eq) was added and stirring continued for 30 minutes. Water (25 vol) was then added and the mixture stirred for 2 hours. The precipitated solid was filtered, washed with water (2×5 vol) and dried under vacuum at 50° C.
Molar Yield=70-75%
Purity by HPLC=99%

Stage 3: Purification of Crude Vorinostat

Aqueous ammonia (2.5 vol) was added to the crude vorinostat (1 eq) in acetonitrile (15 vol) at 25-30° C. The mixture was then maintained at 55-60° C. for 1 hour before being cooled to 20-25° C. and being stirred for a further hour. The resulting solid was filtered, washed with acetonitrile (2×0.5 vol) and dried under vacuum at 45-50° C. for 5 hours.
Molar Yield=55-60%
Purity by HPLC≥99.8%

EXAMPLE 2

Stage 1: Conversion of Suberic Acid to Crude Vorinostat

A mixture of CDI (0.5 eq) and DCC (0.8 eq) in THF (15 vol) was stirred for 1 hour at 25-30° C. Suberic acid (1 eq) and hydroxylamine (1 eq) in THF (1 vol) was added and the mixture stirred for a further 1 hour. Then CDI (0.5 eq), DCC (0.8 eq) and aniline (1 eq) were added to the mixture and the mixture was stirred for a further 16-20 hours. The solid by-product was removed by filtration and the filtrate was concentrated in vacuo at 50° C. to obtain crude vorinostat.

Molar Yield=55-60%
Purity by HPLC≥95.8%

Stage 2: Purification of Crude Vorinostat

Aqueous ammonia (2.5 vol) was added to the crude vorinostat (1 eq) in acetonitrile (15 vol) at 25-30° C. The mixture was then maintained at 55-60° C. for 1 hour before being cooled to 20-25° C. and being stirred for a further hour. The resulting solid was filtered, washed with acetonitrile (2×0.5 vol) and dried under vacuum at 45-50° C. for 5 hours.

Molar Yield=35-40%
Purity by HPLC≥99.8%

It will be understood that the present invention has been described above by way of example only. The examples are not intended to limit the scope of the invention. Various modifications and embodiments can be made without departing from the scope and spirit of the invention, which is defined by the following claims only.

The invention claimed is:

1. A process for the preparation of vorinostat comprising:
   (a') reacting suberic acid with hydroxylamine, or a salt thereof, to form N-hydroxy-7-carboxy-heptanamide; and
   (b') reacting the N-hydroxy-7-carboxy-heptanamide formed in step (a') with aniline, or a salt thereof.

2. The process according to claim 1, wherein:
   (i) step (a') involves a coupling agent; and/or
   (ii) step (a') involves a coupling agent selected from 1,3-dicyclohexylcarbodiimide (DCC); 1,1'-carbonyldiimidazole (CDI); 1-ethyl-3-(3-dimethylaminopropyl)-carbodiimide hydrochloride (WSC.HCl); 1,3-diisopropylcarbodiimide (DIC); or a mixture thereof; and/or
   (iii) step (a') involves a coupling agent, wherein the coupling agent is 1,1'-carbonyldiimidazole (CDI); and/or
   (iv) step (a') involves a coupling agent, and wherein the total amount of coupling agent used in step (a') with respect to the suberic acid is between 1 to 5 molar equivalents; and/or
   (v) step (a') is carried out in an organic solvent; and/or
   (vi) step (a') is carried out in an organic solvent selected from dimethylformamide (DMF), tetrahydrofuran (THF), dichloromethane (DCM), acetonitrile, 1,2-dichlorobenzene, ethanol, or a mixture thereof; and/or
   (vii) step (a') is carried out in DMF; and/or
   (viii) in step (a') hydroxylamine is used in the form of a salt; and/or
   (ix) in step (a') hydroxylamine is used in the form of the hydrochloride salt; and/or
   (x) the total amount of hydroxylamine, or its salt, used in step (a') with respect to the suberic acid is about 1 molar equivalent; and/or
   (xi) step (a') is carried out at a temperature of between 10-60° C.

3. The process according to claim 1, wherein:
   (i) step (b') involves a coupling agent; and/or
   (ii) step (b') involves a coupling agent selected from 1,3-dicyclohexylcarbodiimide (DCC); 1,1'-carbonyldiimidazole (CDI); 1-ethyl-3-(3-dimethylaminopropyl)-carbodiimide hydrochloride (WSC.HCl); 1,3-diisopropylcarbodiimide (DIC); or a mixture thereof; and/or
   (iii) step (b') involves a coupling agent, wherein the coupling agent is a mixture of 1,3-dicyclohexylcarbodiimide (DCC) and 1,1'-carbonyldiimidazole (CDI); and/or
   (iv) step (b') involves a coupling agent, wherein the coupling agent is a mixture of 1,3-dicyclohexylcarbodiimide (DCC) and 1,1'-carbonyldiimidazole (CDI), and wherein the mixture of CDI and DCC is in a molar ratio range of 0.1:10 to 10:0.1 CDI:DCC; and/or
   (v) step (b') involves a coupling agent, and wherein the total amount of coupling agent used in step (b') with respect to the N-hydroxy-7-carboxy-heptanamide is between 1 to 5 molar equivalents; and/or
   (vi) step (b') is carried out in an organic solvent; and/or
   (vii) step (b') is carried out in an organic solvent selected from dimethylformamide (DMF), tetrahydrofuran (THF), dichloromethane (DCM), acetonitrile, 1,2-dichlorobenzene, ethanol, or a mixture thereof; and/or
   (viii) step (b') is carried out in THF; and/or
   (ix) step (b') is carried out at a temperature of between 10-60° C.

4. The process according to claim 1, wherein:
   (i) step (a') and step (b') are carried out in the same organic solvent; and/or
   (ii) step (a') and step (b') are carried out in the same organic solvent selected from dimethylformamide (DMF), tetrahydrofuran (THF), dichloromethane (DCM), acetonitrile, 1,2-dichlorobenzene, ethanol, or a mixture thereof; and/or
   (iii) step (a') and step (b') are carried out in the same organic solvent selected from THF, DMF, or a mixture thereof; and/or
   (iv) an activating agent is used in step (a') and/or step (b'); and/or
   (v) an activating agent is used in step (a') and/or step (b'), and wherein the activating agent is selected from cyanuric chloride, cyanuric fluoride, catecholborane, or a mixture thereof; and/or
   (vi) vorinostat is obtained with an HPLC purity of more than 99%.

5. The process according to claim 1, further comprising the step of isolating vorinostat.

6. The process according to claim 5, wherein the vorinostat has an HPLC purity of more than 99%.

7. The process according to claim 6, wherein the substantially pure vorinostat has an HPLC purity of more than 99.5%.

8. The process according to claim 5, further comprising the step of combining the vorinostat with one or more pharmaceutically acceptable excipient(s) to provide a pharmaceutical composition comprising vorinostat and one or more pharmaceutically acceptable excipient(s).

9. The process according to claim 8, further comprising the step of administering to a patient in need thereof a therapeutically effective amount of the pharmaceutical composition to treat cancer and/or skin cancer and/or cutaneous T-cell lymphoma (CTCL).

10. Vorinostat as prepared by a process according to claim 1.

11. Vorinostat according to claim 10, wherein the vorinostat has an HPLC purity of more than 99%.

* * * * *